(12) United States Patent
Murphy (10) Patent No.: US 7,563,237 B1
(45) Date of Patent: Jul. 21, 2009

(54) CRANIAL CORRECTION ORTHOSES

(76) Inventor: James David Murphy, 11650 W. 139th St., Orland Park, IL (US) 60467

( * ) Notice: Subject to any disclaimer, the term of this patent is extended or adjusted under 35 U.S.C. 154(b) by 235 days.

(21) Appl. No.: 11/151,504

(22) Filed: Jun. 13, 2005

(51) Int. Cl.
- A61F 5/00 (2006.01)
- A61F 11/00 (2006.01)
- A61F 7/00 (2006.01)
- A42B 1/06 (2006.01)

(52) U.S. Cl. ............ 602/17; 602/5; 602/1; 128/857; 128/858; 128/97.1; 128/112.1; 128/121.1; 2/410; 2/424; 2/411; 2/421; 607/108; 607/109; 607/110

(58) Field of Classification Search ............ 602/17, 602/5, 1; 128/857, 858, 121.1, 112.1, 97.1; 606/53, 54; 2/410, 423, 411, 421, 417–420, 2/183, 909; 607/108, 109, 110
See application file for complete search history.

(56) References Cited

U.S. PATENT DOCUMENTS

| | | | |
|---|---|---|---|
| 4,161,946 A * | 7/1979 | Zuesse | 602/36 |
| 4,776,324 A | 10/1988 | Clarren | |
| 5,094,229 A * | 3/1992 | Pomatto et al. | 602/17 |
| 5,549,678 A | 8/1996 | Prostkoff | |
| 5,673,431 A * | 10/1997 | Batty | 2/9 |
| 5,809,573 A * | 9/1998 | Bary | 2/209 |
| 5,993,448 A | 11/1999 | Remmler | |
| RE36,583 E | 2/2000 | Pomatto et al. | |
| 6,036,690 A | 3/2000 | De La Plaza Fernandez | |
| 6,381,760 B1 * | 5/2002 | Lampe et al. | 2/425 |
| 6,428,494 B1 * | 8/2002 | Schwenn et al. | 602/17 |
| 6,592,536 B1 | 7/2003 | Argenta | |
| 2003/0145384 A1 * | 8/2003 | Stelnicki | 5/655 |
| 2004/0015118 A1 * | 1/2004 | Sklar et al. | 602/74 |
| 2005/0193477 A1 * | 9/2005 | Penny | 2/411 |

FOREIGN PATENT DOCUMENTS

| | | |
|---|---|---|
| JP | 9253090 | 9/1997 |
| SU | 735.247 | 5/1980 |
| SU | 1.718.860 | 3/1992 |

OTHER PUBLICATIONS http://www.ballert.com.

* cited by examiner

Primary Examiner—Patricia Bianco
Assistant Examiner—Tarla Patel
(74) Attorney, Agent, or Firm—Michael I Kroll

(57) ABSTRACT

Apparatus 10 discloses a cranial orthosis for treating cranial deformities in infants. The device 10 conforms to the contour of an infant's head 18 and is used to correct positional plagiocephaly by redirecting the compressive forces that would otherwise be imposed on soft, compliant areas of the developing cranium. The device 10 is comprised of a frame member 12 housing having front 14 and rear 16 pads incorporating means for adjusting pressure 24 thereon. The cranial orthosis 10 has at least one removable panel 44 for relieving pressure during nighttime use. Alternate embodiments disclose devices having three pads 14, 54 in either an "X" or "Y" configuration.

3 Claims, 13 Drawing Sheets

CRANIAL CORRECTION ORTHOSES

BACKGROUND OF THE INVENTION

1. Field of the Invention

The present invention relates generally to orthoses and, more specifically, to a cranial orthosis for treating cranial deformities in infants.

The device conforms to the contour of an infant's head and is used to correct positional plagiocephaly by redirecting the compressive forces that would otherwise be imposed on soft, compliant areas of the developing cranium. The device is comprised of a housing having front and rear pads incorporating means for adjusting pressure thereon. The cranial orthosis has at least one removable panel for relieving pressure during nighttime use.

2. Description of the Prior Art

There are other cranial device designed for cranial support. Typical of these is U.S. Pat. No. 4,776,324 issued to Clarren on Oct. 11, 1988.

Another patent was issued to Pomatto et al. on Mar. 10, 1992 as U.S. Pat. No. 5,094,229. Yet another U.S. Pat. No. 5,549,678 was issued to Prostkoff on Aug. 27, 1996 and still yet another was issued on Nov. 30, 1999 to Remmler as U.S. Pat. No. 5,993,448.

Another patent was issued to Pomatto et al. on Feb. 22, 2000 as U.S. Pat. No. Re. 36,583. Yet another U.S. Pat. No. 6,036,690 was issued to De La Plaza Fernandez on Mar. 14, 2000. Another was issued to Argenta on Jul. 15, 2003 as U.S. Pat. No. 6,592,536 and still yet another was filed on Jan. 22, 2004 to Sklar et al. as U.S. Patent Application No. 2004/0015118.

Another patent was issued to Kvaskov et al. on Mar. 25, 1980 as Soviet Union Patent No. SU735247. Yet another Soviet Patent No. SU1718860 was issued to Levchenko et al. on Mar. 15, 1992. Another was issued to Yasuhiro on Sep. 30, 1997 as Japanese Patent No. JP9253090.

U.S. Pat. No. 4,776,324

Inventor: Sterling K. Clarren

Issued: Oct. 11, 1988

A method of helmet treatment for deformational cranial asymmetry in which the dimensions of the therapeutic helmet cavity are prescribed in relation to specific CT scan sections of the plagiocaphalic infant's cranium. A graded series of sized helmets is provided for such treatments. Each helmet cavity is configured to accommodate and effectively treat infants of specified ages and degrees of plagiocephaly. By employing the subject off-the-shelf helmets, the time-consuming and labor-intensive fitting of individualized helmets is obviated.

U.S. Pat. No. 5,094,229

Inventor: Jeanne K. Pomatto et al.

Issued: Mar. 10, 1992

A cranial remodeling band has an internal surface shaped to the configuration to which a subject's cranium is to be reconfigured. The band has at least one discontinuity therein permitting relative movement of anterior and posterior portions of the band. An elastic member extending across the discontinuity biases the anterior and posterior regions toward each other.

U.S. Pat. No. 5,549,678

Inventor: Melvin E. Prostkoff

Issued: Aug. 27, 1996

An external cranial protective device which provides a protective and aesthetically pleasing function in protecting the brain of an individual where a section of the bone has been removed from the skull or face.

U.S. Pat. No. 5,993,448

Inventor: Daniel J. Remmler

Issued: Nov. 30, 1999

An apparatus for relative movement of first and second bone segments, such as segments of a skull, includes first and second nodes attachable to first and second bone segments, respectively, and a first rod mechanism flexibly attached to both the first and second nodes. The rod mechanism is either extendible or retractable along an axis thereof. The rod mechanism axis is pivotable with respect to the first and second nodes in at least a first plane parallel to a plane tangent to the skull. The rod mechanism axis also is pivotable with respect to the first and second nodes in a second plane perpendicular to the first plane.

U.S. Pat. No. Re. 36,583

Inventor: R. Craig Pomatto et al.

Issued: Feb. 22, 2000

A cranial remodeling orthosis is shaped to extend across the top of the head with depending regions closely confining the temporal bone regions and the mastoid process regions of the cranium. The orthosis is self-suspending and preferably includes an elastic band for imparting ear-to-ear rigidity to the device.

U.S. Pat. No. 6,036,690

Inventor: Rafael De La Fernandez

Issued: Mar. 14, 2000

Linear expander for progressive correction of craniofacial deformations. It consists in two elements which are movable longitudinally with respect to one another, are driven by an actuating element arranged between them and are intended to cause mutual displacement of the portions of tissue to which they are applied by means of the injection of a fluid. The expander also comprises an inflatable element, made of flexible and elastic material, which actuates a movable element adapted to cause separation of the bony tissue to which it is applied from the remainder of the bony tissue anchored to the fixed element of the expander. Said movable element has its free end shaped as a hook in order to be applied under the edge of the portion of bony tissue opposite that in which the fixed element, which may have a similar hook, is anchored.

U.S. Pat. No. 6,592,536

Inventor: Louis C. Argenta

Issued: Jul. 15, 2003

A method and apparatus for treating infant plagiocephaly whereby a helmet encircles the upper cranium of an infant and prevents the infant from resting its head on flattened or depressed regions of the skull. The helmet contemplates an adjustable first member which encircles the infant's upper cranium, and a second member comprising a relatively rigid protruding element that is attached to the exterior surface of the first member. The second member is positioned so that it is superincumbent to flattened or depressed regions, so that when the helmet is worn, the second member forces the infant to rest its head on a different area of the skull, thus passively relieving pressure on the depressed skull, and applying a gentle active pressure to other areas. Additionally, the method an apparatus relates to the treatment of torticollis and other abnormalities of the neck.

U.S. Patent Application Number 2004/0015118

Inventor: Frederick H. Sklar

Issued: Jan. 22, 2004

A cranial orthosis is contoured to match the curvature of the fronto-temporal, parietal and occipital areas of an infant's cranial vault to provide protection against the acquisition of postural cranial deformities as a result of the infant's sleeping in the supine position. The orthosis is designed to be of universal fit, as determined by the infant's fronto-occipital head circumference (FOC) measurement. Moreover, the interior dimensions of the orthosis can be enlarged to accommodate growth of the infant's head without requiring replacement. The orthosis is a molded plastic appliance in the form of a shell, headband or helmet having interior surfaces that are smoothly contoured to conform in shape to the surface curvature of the occipital, temporal and parietal areas of a healthy human infant having normal cranium size, shape and symmetry. The cavity is sized to provide a close, non-interfering fit of the conformed interior surfaces in facing relation to the occipital, fronto-temporal and parietal areas of the infant's cranial vault, thereby allowing the infant's head weight forces to spread substantially uniformly across one or more of the conformed interior surfaces while the infant is resting on a sleep surface in the supine position.

Soviet Union Patent Number 735247

Inventor: Stalvek M. Kvaskov

Issued: May 25, 1980

The invention discloses an apparatus for treating cranium fractures.

Soviet Union Patent Number SU1718860

Inventor: Aleksandr R Levchenko et al.

Issued: Mar. 15, 1992

The invention discloses a device for treating fractures and deformities of visceral cranium bones.

Japanese Patent Number JP735247

Inventor: Goto Yasuhiro

Issued: Sep. 30, 1997

PROBLEM TO BE SOLVED: To easily and surely fix a head part.

SOLUTION: Among the four pieces of fixing pin units 14 and 15 attached to a fixed frame 11, the fixing pin units 14 on a face side for fixing the head part A of a patient from the face side are capable of turning adjustment in the direction of an arrow X with a holder 18 extended in the thickness direction of the fixed frame 11 as a center and the fixing pin units 15 on a rear head part side for fixing the head part A from the rear head part side are incapable of the turning adjustment. In the case of fixing the head part A, since the fixing pins 22 of the fixing pin units 15 on the rear head part side are not turned, the rear head part side is surely fixed. Then, since the fixing pins 22 of the fixing pin units 14 on the face side are capable of the turning adjustment, by adjusting the fixing pins 22 to positions suitable for fixation, the head part A is easily and surely fixed.

While these cranial devices may be suitable for the purposes for which they were designed, they would not be as suitable for the purposes of the present invention, as hereinafter described.

SUMMARY OF THE PRESENT INVENTION

The present invention discloses a cranial orthosis for treating cranial deformities in infants. The device conforms to the contour of an infant's head and is used to correct positional plagiocephaly by redirecting the compressive forces that would otherwise be imposed on soft, compliant areas of the developing cranium. The device is comprised of a frame member housing having front and rear pads incorporating means for adjusting pressure thereon. The cranial orthosis has at least one removable panel for relieving pressure during nighttime use.

A primary object of the present invention is to provide a cranial orthosis for treatment of cranial deformations.

Another object of the present invention is to provide a cranial orthosis having spaced apart pads with means for adjusting said spacing.

Yet another object of the present invention is to provide a cranial orthosis having a removable panel.

Additional objects of the present invention will appear as the description proceeds.

The present invention overcomes the shortcomings of the prior art by providing a cranial orthosis that conforms to the contour of an infants head and is used to prevent positional plagiocephaly by redirecting the compressive forces that would otherwise be imposed on soft, compliant areas of the developing cranium. The device is comprised of a housing having front and rear pads incorporating means for adjusting pressure thereon. The cranial orthosis has at least one removable panel for relieving pressure during nighttime use.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

With regard to reference numerals used, the following numbering is used throughout the drawings.

10 present invention
12 frame member
14 front pad
16 rear pad
18 head
20 mating band
22 mating band
24 tensioning member
26 attachment means
27 attachment means
28 anterior
30 posterior
32 fontenal
34 squamsosal suture
36 sagital suture
38 lambdoid suture
40 coronal suture
42 occiput
44 removable panel
46 deformity
48 strap
50 strap
52 strap
54 lateral pad
56 Y design
58 space

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments since practitioners skilled in the art will recognize numerous other embodiments as well. For a definition of the complete scope of the invention, the reader is directed to the appended claims.

Figure 1:
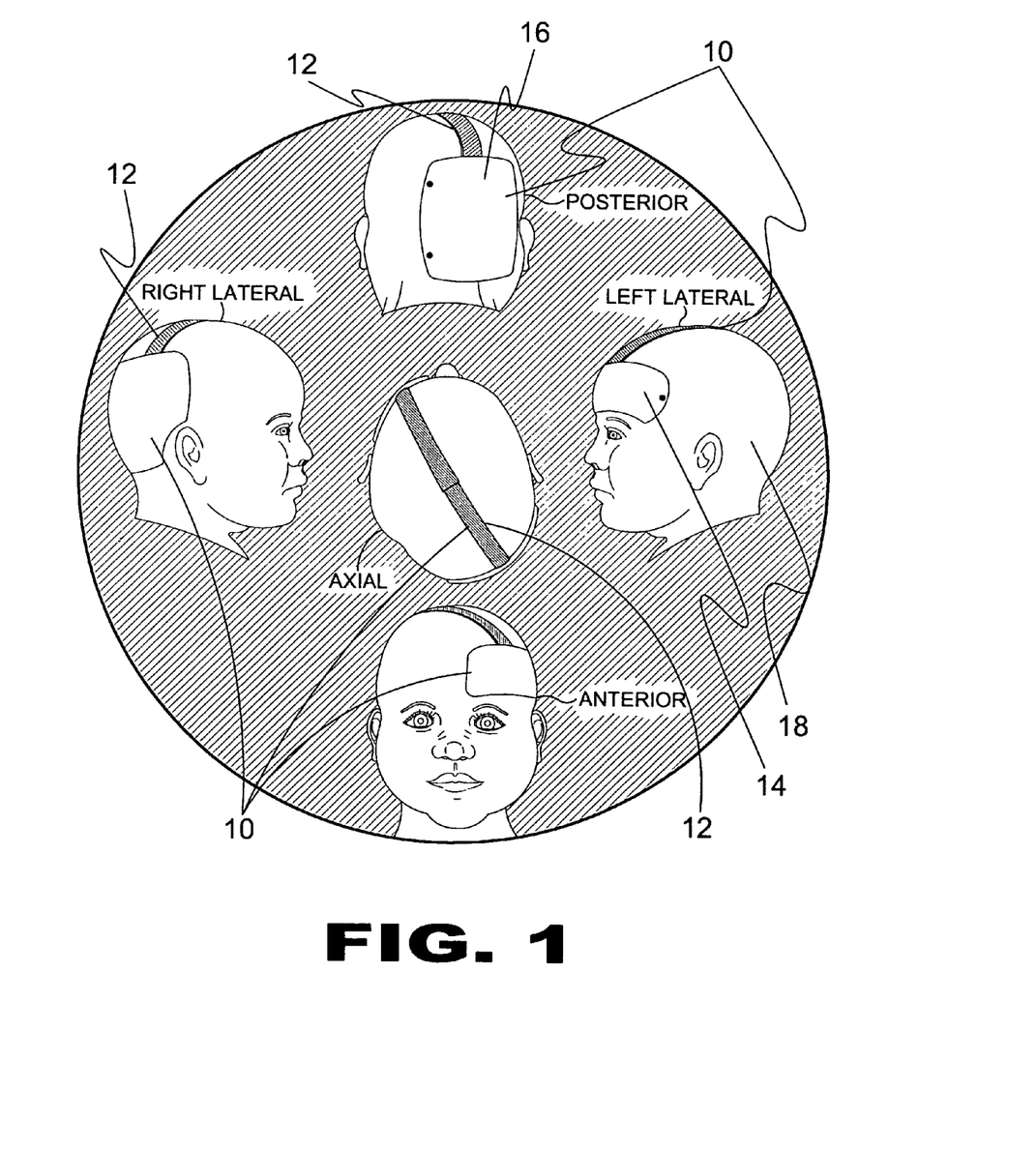
FIG. 1 is an illustrative view of the application of the present invention.

Turning to FIG. 1, shown therein is an illustrative view of the application of the present invention 10. The cranial orthoses of the present invention 10 are used for treating cranial deformities in infants through application of a frame member 12 having appropriately positioned front 14 and rear 16 pads with means for varying pad pressure and means for releasably attaching a panel between the pads. Various alternate frame configurations are illustrated to demonstrate method and apparatus whereby the apparatus is designed to conform to the contour of an infant's head 18 and is used to correct positional plagiocephaly by redirecting the compressive forces that would otherwise be imposed on soft, compliant areas of the developing cranium. In one embodiment, the device 10 is comprised of a frame 12 having front 14 and rear 16 pads incorporating means for adjusting pressure thereon. The cranial orthosis 10 includes at least one removable panel that provides for greater heat dissipation during daytime use with selective attachment of the panel during sleep to keep pressure off the deformity allowing maximum correction.

Figure 2:
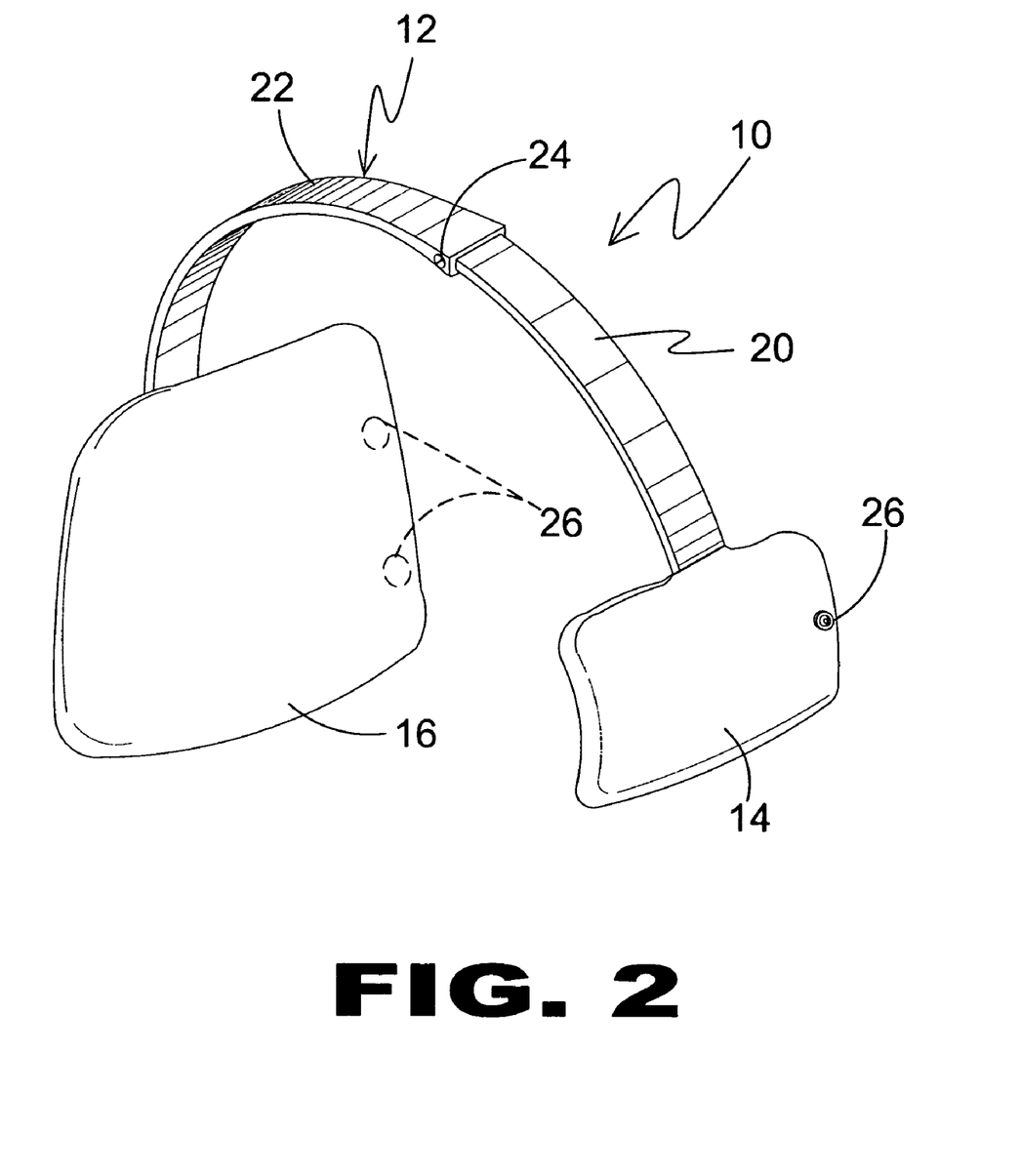
FIG. 2 is a perspective view of a curvilinear cranial orthosis.

Turning to FIG. 2, shown therein is a perspective view of a curvilinear cranial orthosis 10. Shown is the cranial orthosis 10 comprised of slidably engaging bands 20, 22 forming a length adjustable frame 12 terminating in pads 14, 16 with the bands incorporating a tensioning member 24, e.g., a set screw for selectively varying pad pressure upon the cranium/pad points of engagement. Frame 12 is effectively resilient to provide the correct pressure to the cranium. The bands 20, 22 are contoured to substantially match the curvature of an infant's cranium to correct postural cranial deformities. The device 10 is comprised of engaging frame members 20, 22, pads 14, 16 and selectively attachable panel that provides for greater heat dissipation during daytime use with selective attachment of the panel during sleep to keep pressure off the deformity allowing maximum correction. Also shown are attachment means 26, e.g., mating male and female snaps.

Figure 3:
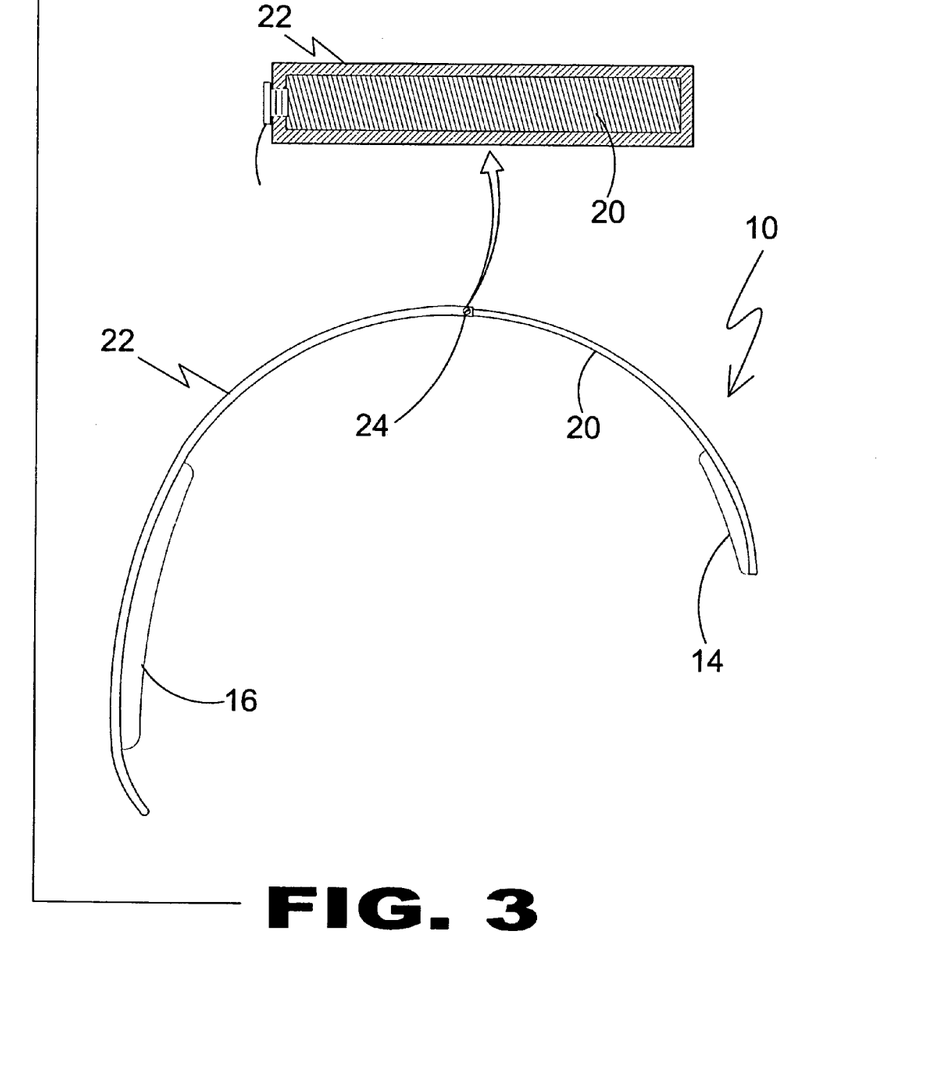
FIG. 3 is a front view of the curvilinear cranial orthosis.

Turning to FIG. 3, shown therein is a front view of the curvilinear cranial orthosis 10. Shown is the cranial orthosis 10 comprised of slidably engaging bands 20,22 terminating in pads 14,16 with the bands incorporating a tensioning member 24 at the point of juncture of the bands for selectively varying pad pressure upon the cranium/pad points of engagement. The bands 20, 22 may have a rectangular cross-section and may have male and female telescoping members and are contoured to match the curvature of an infant's cranium to correct postural cranial deformities. The device 10 is comprised of engaging frame members 20, 22, pads 14, 16 and selectively attachable panel that provides for greater heat dissipation during daytime use with selective attachment of the panel during sleep to keep pressure off the deformity allowing maximum correction.

Figure 4:
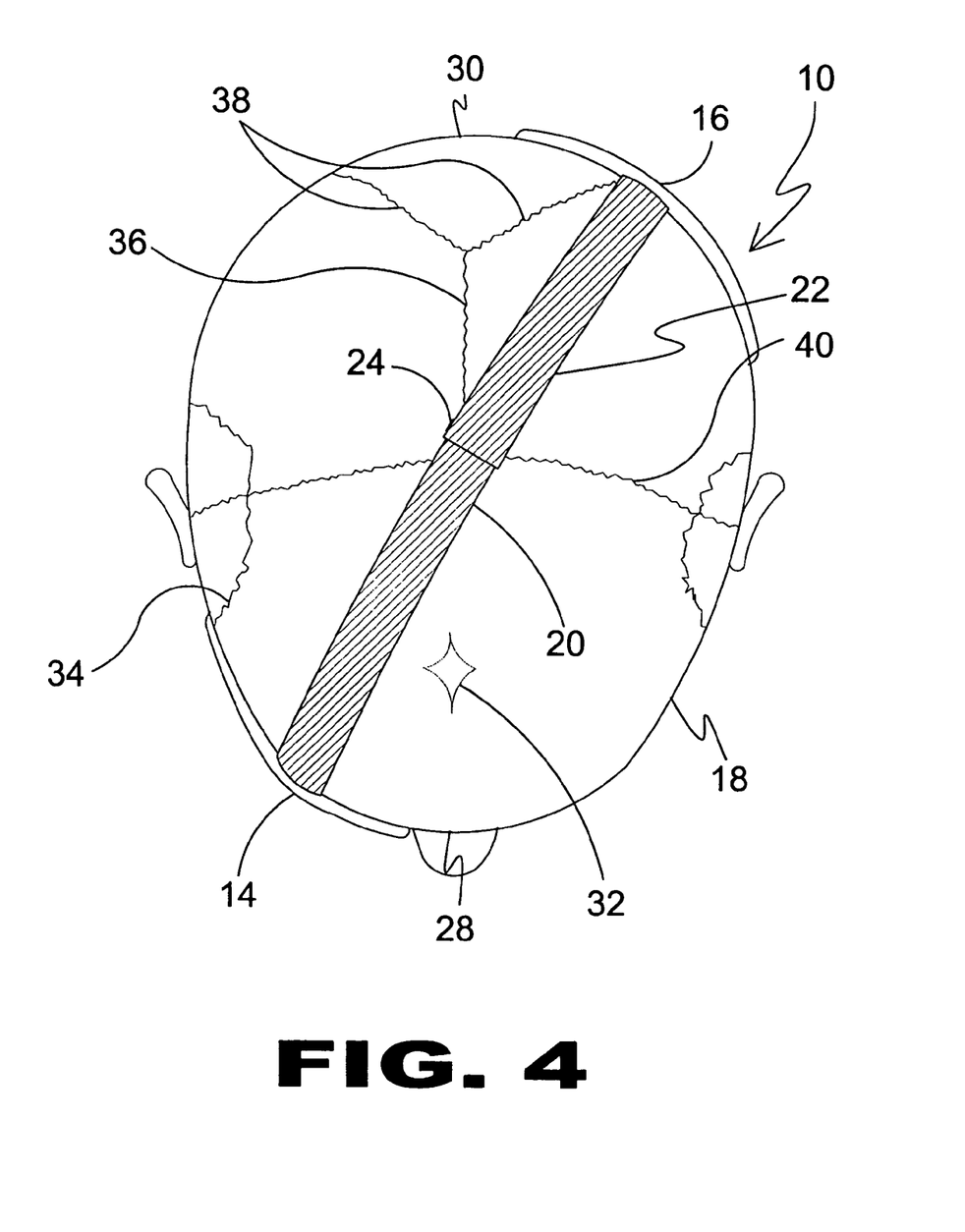
FIG. 4 is a top view of the curvilinear cranial orthosis with opposing pads.

Turning to FIG. 4, shown therein is a top view of the curvilinear cranial orthosis 10 with opposing pads. The cranial orthosis 10, used for treating cranial deformities in infants, has a pair of slidably engaging bands 20, 22 terminating in pads 14, 16 that are moved until engaging the cranium with the desired pressure whereupon the tensioning member 24 is releasably fastened. Extending from the pads 14, 16 are a plurality of fasteners whereby a panel having mating fastener members that when attached forms a shell encompassed by the pads. Various alternate frame configurations are forthcoming to demonstrate method and apparatus whereby the apparatus 10 is designed to conform to the contour of an infant's head 18 and is used to correct positional plagiocephaly by redirecting the compressive forces that would otherwise be imposed on soft, compliant areas of the developing cranium. Further incorporated is at least one removable panel that provides for greater heat dissipation during daytime use with selective attachment of the panel during sleep to keep pressure off the deformity allowing maximum correction. Also shown are the anterior 28, posterior 30, fontenal 32, squasmosal suture 34, sagital suture 36, lambdoid suture 38 and coronal suture 40.

Figure 5:
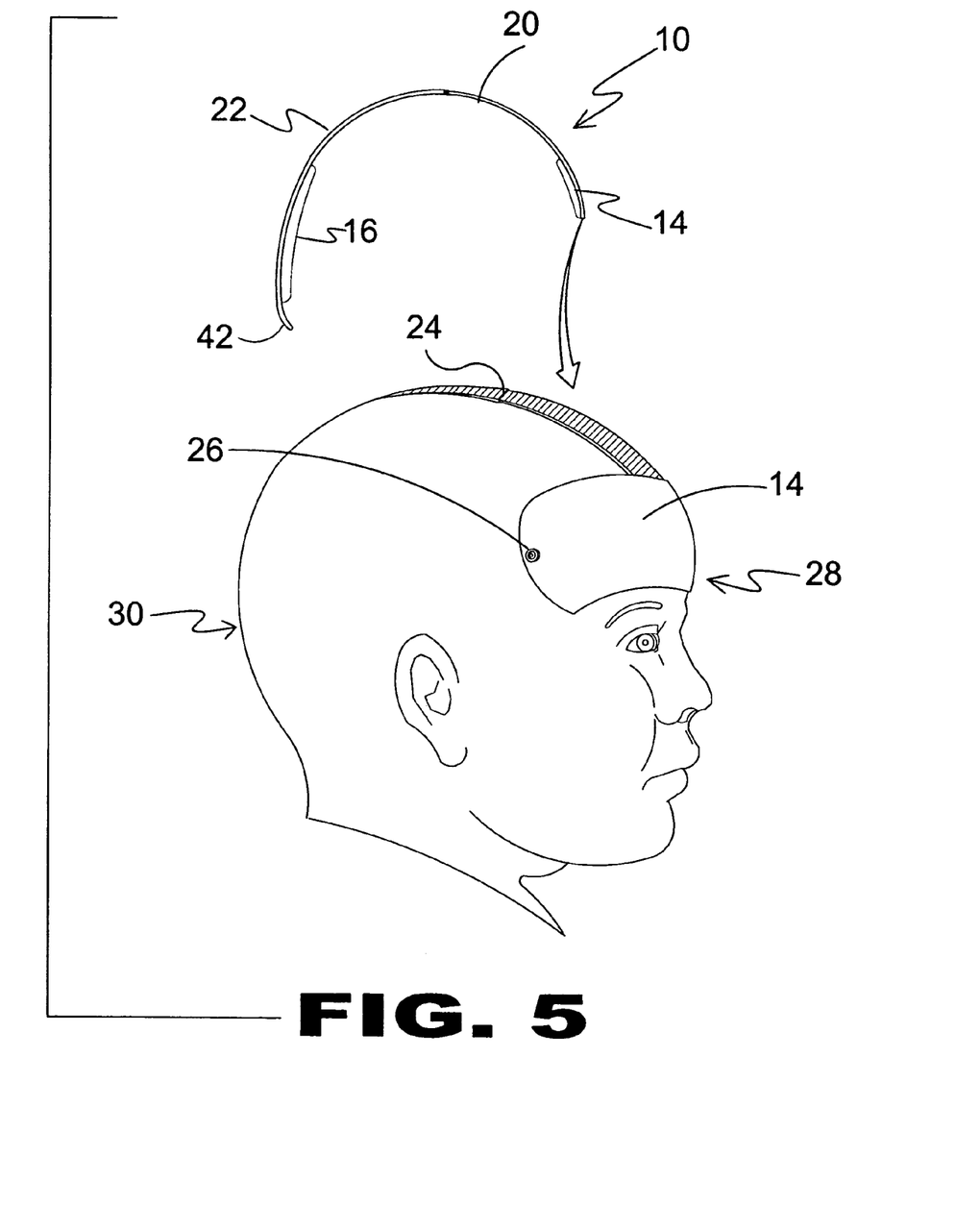
FIG. 5 is a right lateral view of the curvilinear cranial orthosis in use.

Turning to FIG. 5, shown therein is a right lateral view of the curvilinear cranial orthosis 10 in use. Illustrated is a right lateral view of the present invention 10 in use comprising a pair of slidably engaging bands 20, 22 terminating in pads 14, 16 that are moved until engaging the cranium with the desired pressure whereupon the tensioning member 24 is releasably fastened. Additionally a panel can be attached between the pads 14, 16 as desired. Also shown are the anterior 28, posterior 30 and a snap or attachment means 26 and an occiput 42.

Figure 6:
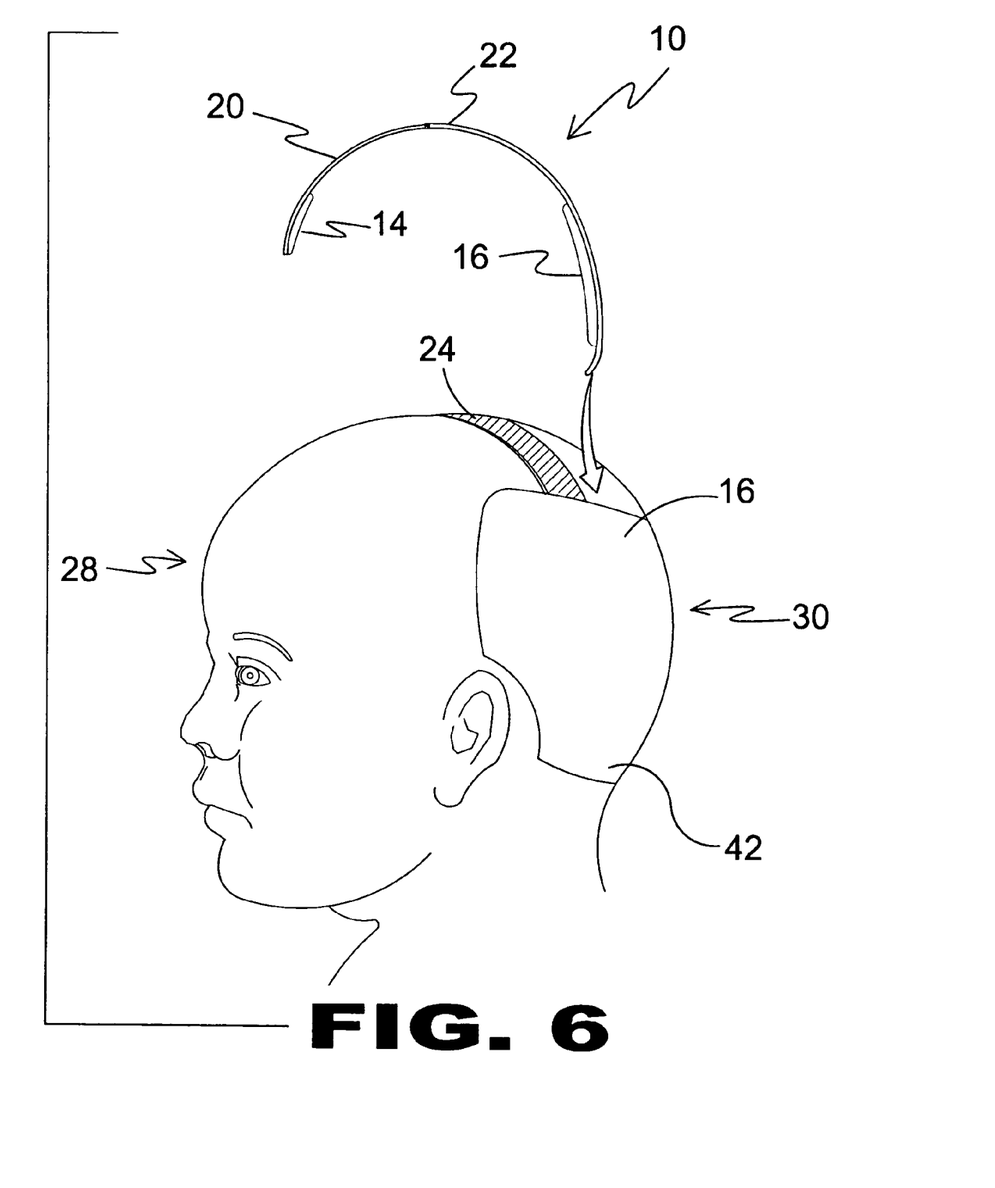
FIG. 6 is a left lateral view of the curvilinear cranial orthosis in use.

Turning to FIG. 6, shown therein is a left lateral view of the curvilinear cranial orthosis 10 in use. Illustrated is a left lateral view of the present invention 10 in use comprising a pair of slidably engaging bands 20, 22 terminating in pads 14, 16 that are moved until engaging the cranium with the desired pressure whereupon the tensioning member 24 is releasably fastened. Additionally a panel can be attached between the pads 14, 16 as desired. Other previously disclosed elements are also shown.

Figure 7:
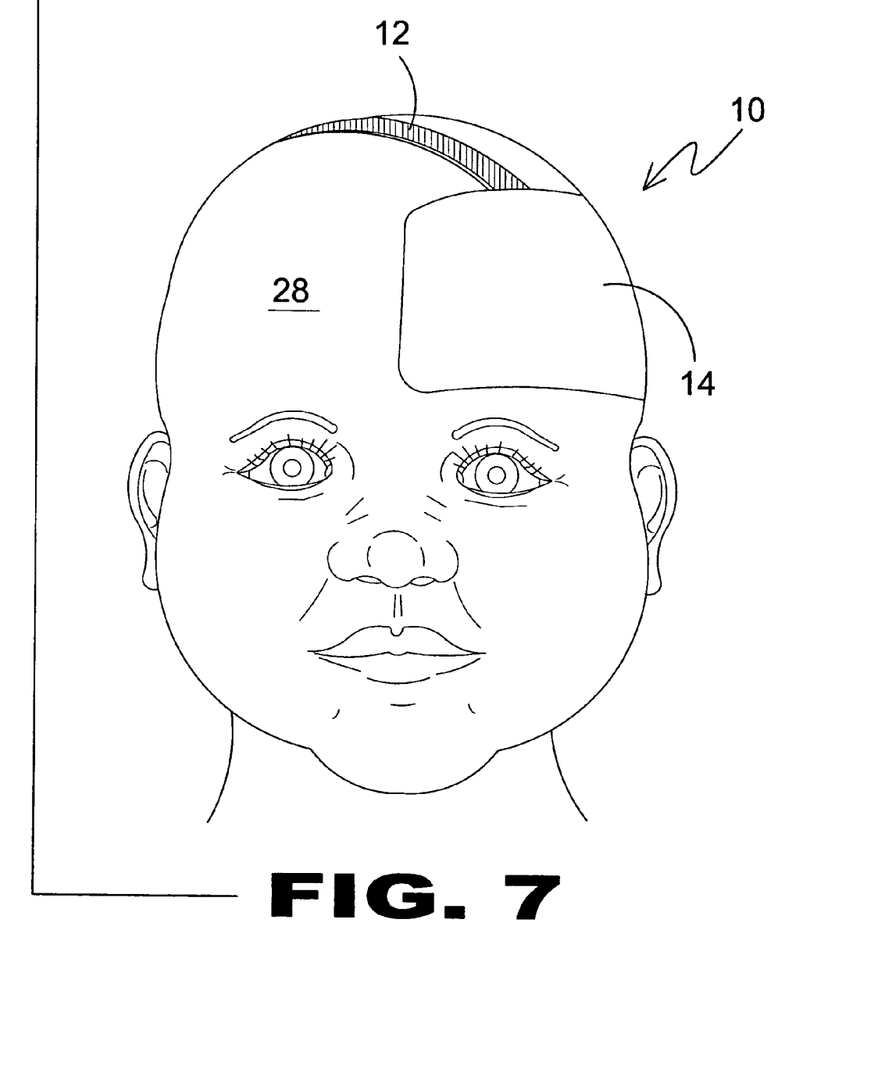
FIG. 7 is an anterior view of the curvilinear cranial orthosis in use.

Turning to FIG. 7, shown therein is an anterior view of the curvilinear cranial orthosis 10 in use. Illustrated is an anterior view of the present invention 10 in use comprising a pair of slidably engaging bands terminating in pads that are moved until engaging the cranium with the desired pressure whereupon the tensioning member is releasably fastened. Additionally a panel can be attached between the pads as desired. Shown are frame 12 and anterior 28, with a front pad 14 covering the protruding portion of the frontal lobe and extending laterally.

Figure 8:
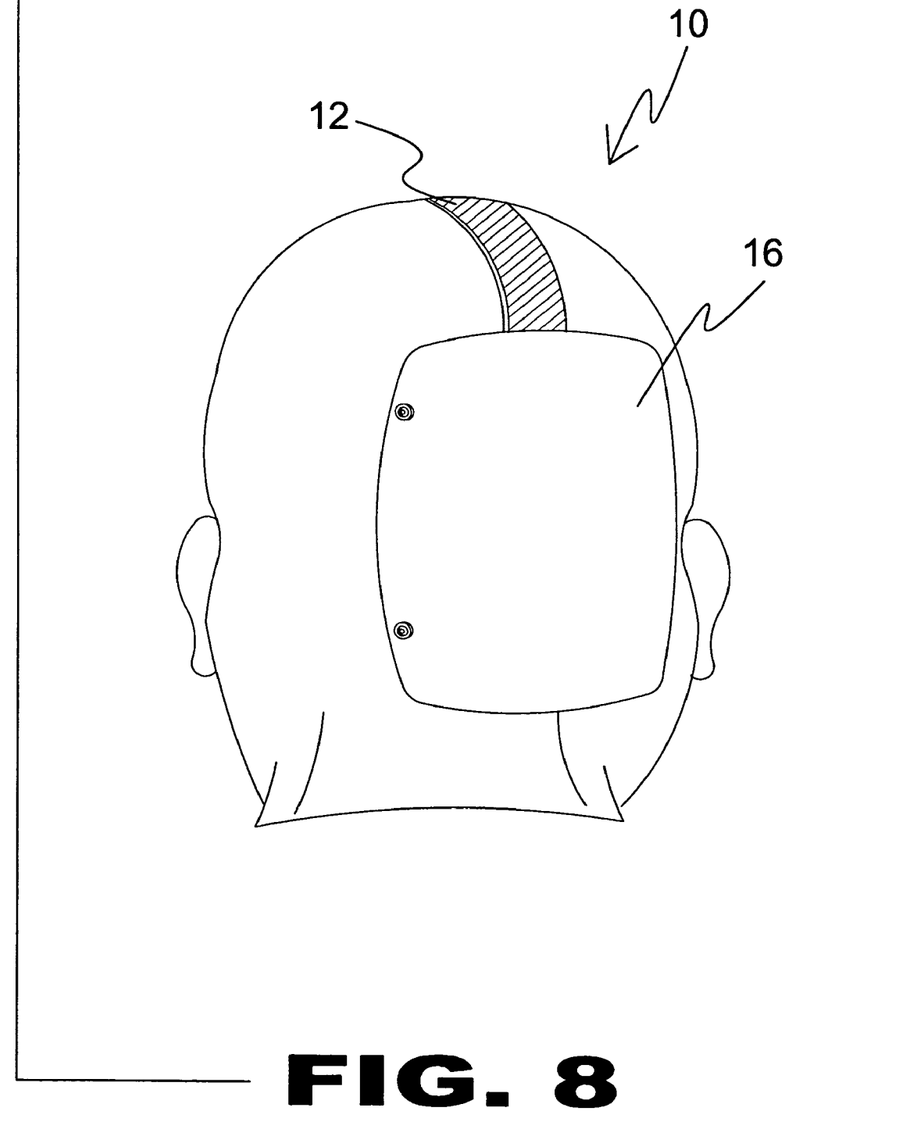
FIG. 8 is a posterior view of the curvilinear cranial orthosis in use.

Turning to FIG. 8, shown therein is a posterior view of the curvilinear cranial orthosis 10 in use. Illustrated is a posterior view of the present invention 10 in use comprising a pair of slidably engaging bands terminating in pads that are moved until engaging the cranium with the desired pressure whereupon the tensioning member is releasably fastened. Additionally a panel can be attached between the pads as desired. Shown are frame 12 and rear pad 16.

Figure 9:
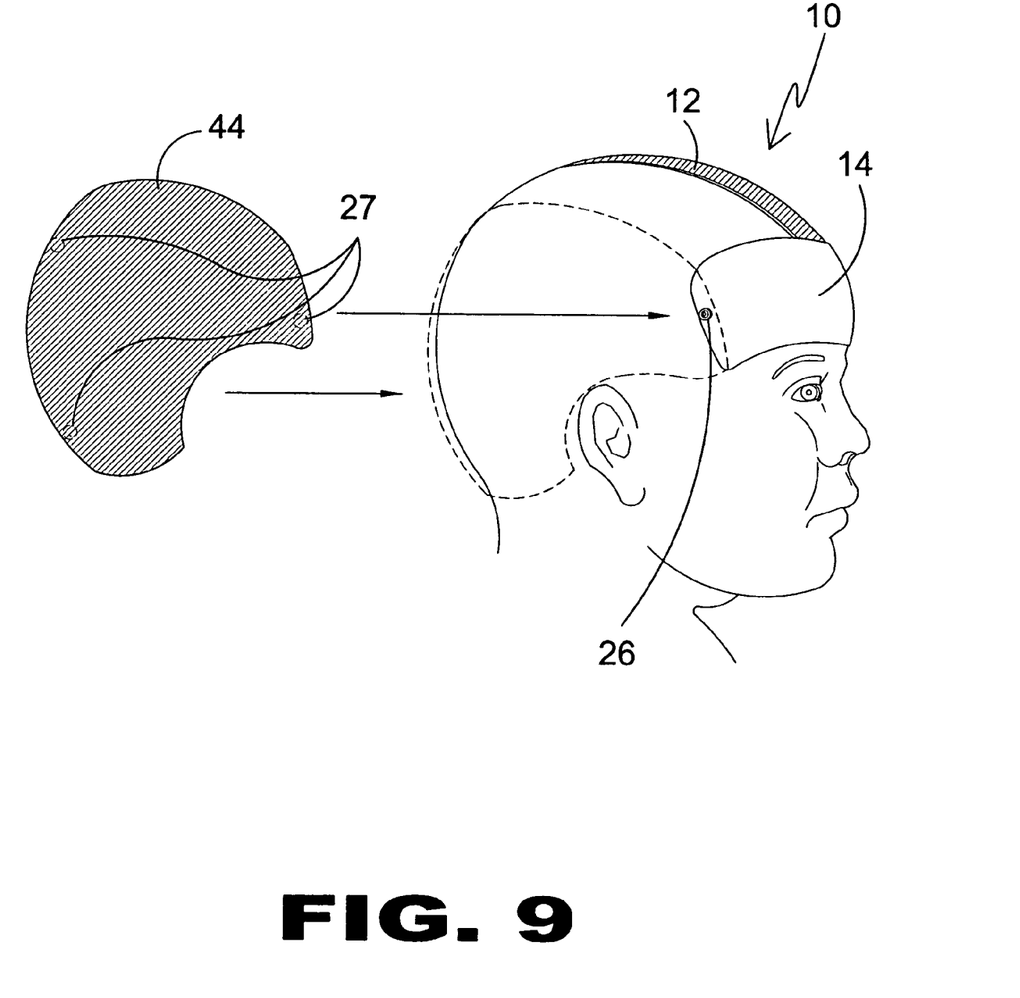
FIG. 9 is a right lateral view of the present invention.

Turning to FIG. 9, shown therein is a right lateral view of the present invention 10. Shown is a right lateral view of the present invention 10 disclosing a cranial orthosis apparatus having at least one removable panel 44 with attachment means 27 that provides for greater heat dissipation during daytime use with selective attachment of the panel during sleep to keep pressure off the deformity allowing maximum correction. Also shown are frame 12 with front pad 14 and mating attachment means 26.

Figure 10:
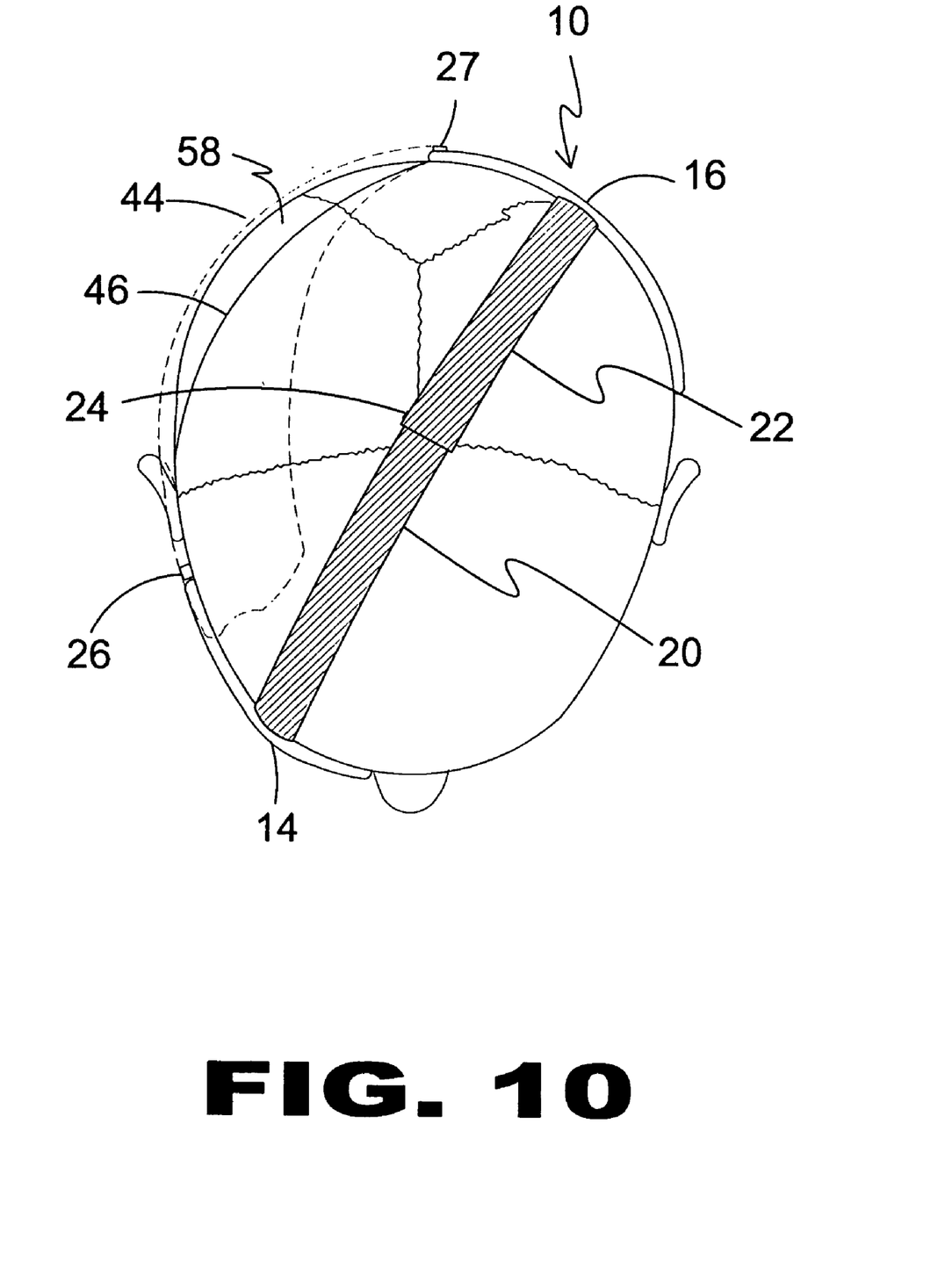
FIG. 10 is a top view of the application of the present invention.

Turning to FIG. 10, shown therein is a top view of the application of the present invention 10. Illustrated is the cranial orthosis 10 having a removable panel 44 that with selective attachment of the panel during sleep provides a space 58 to keep pressure off the area of deformity 46 allowing maximum correction. Other previously disclosed elements are also shown.

Figure 11:
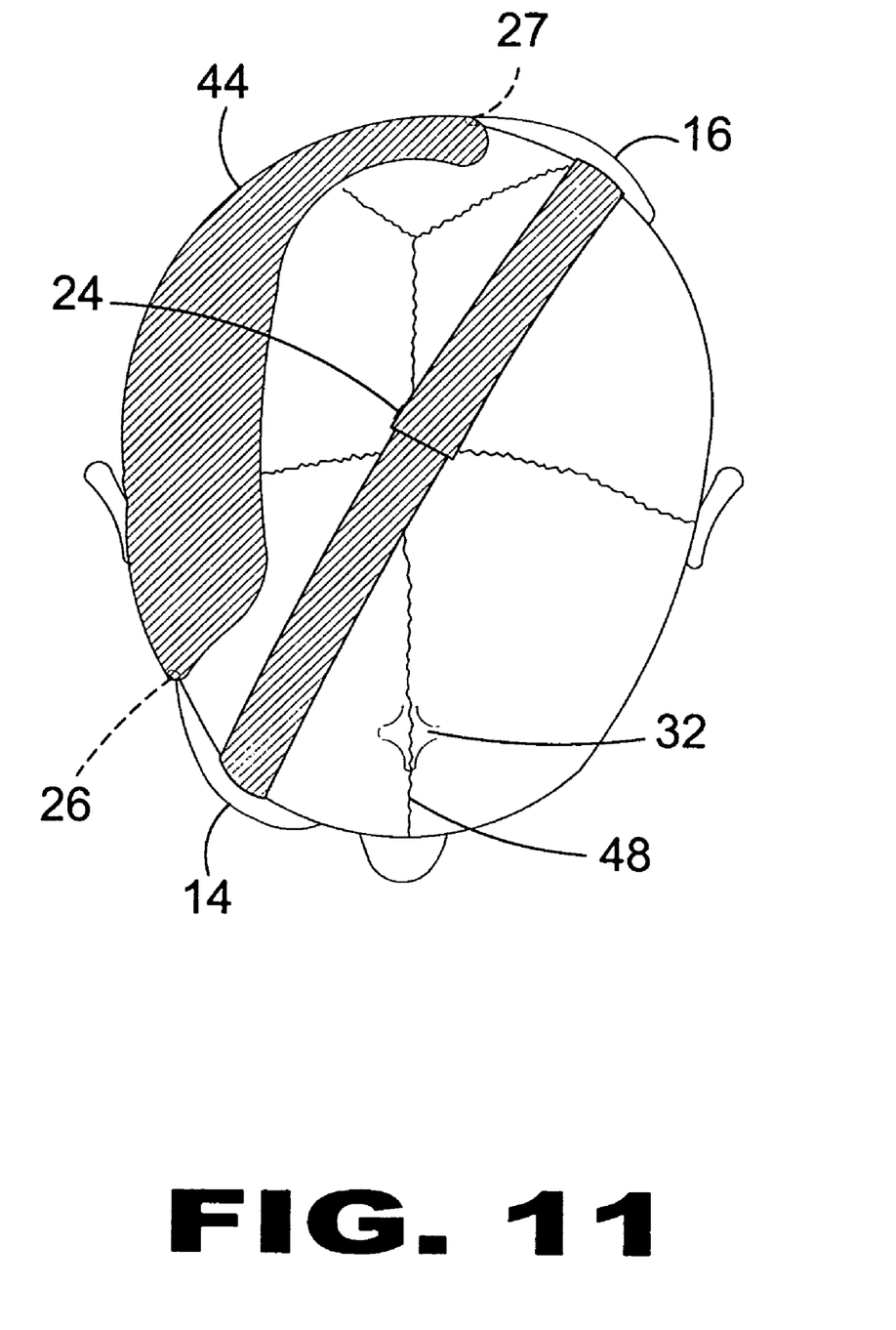
FIG. 11 is a top view of the application of the present invention.

Turning to FIG. 11, shown therein is a top view of the application of the present invention 10. Illustrated is the cranial orthosis having a removable panel 44 that with selective attachment of the panel during sleep keeps pressure off the deformity allowing maximum correction. Also shown are a metatopic suture 48 and other previously disclosed elements.

Figure 12:
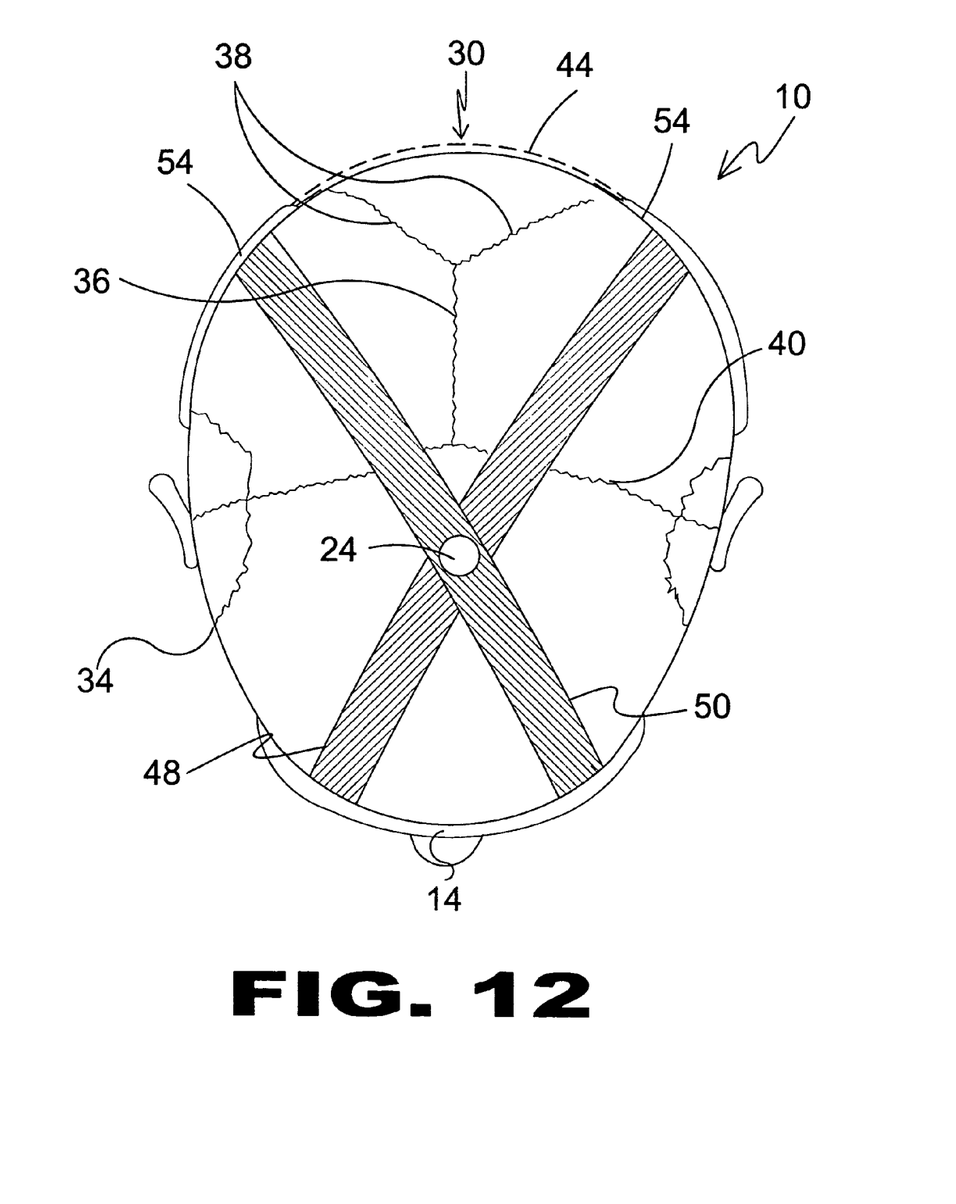
FIG. 12 is a top view of an additional element of the present invention.

Turning to FIG. 12, shown therein is a top view of an additional element of the present invention 10. Shown is a variation having an intersecting pair of straps 48, 50 with pads 14, 16 positioned on each end forming an X-design. The device 10 conforms to the contour of an infant's head and is used to prevent positional plagiocephaly by redirecting the compressive forces that would otherwise be imposed on soft, compliant areas of the developing cranium. The device 10 discloses a cranial orthosis having front 14 and lateral pads 54 incorporating means for adjusting pressure 24 thereon. Other previously disclosed elements are also shown.

Figure 13:
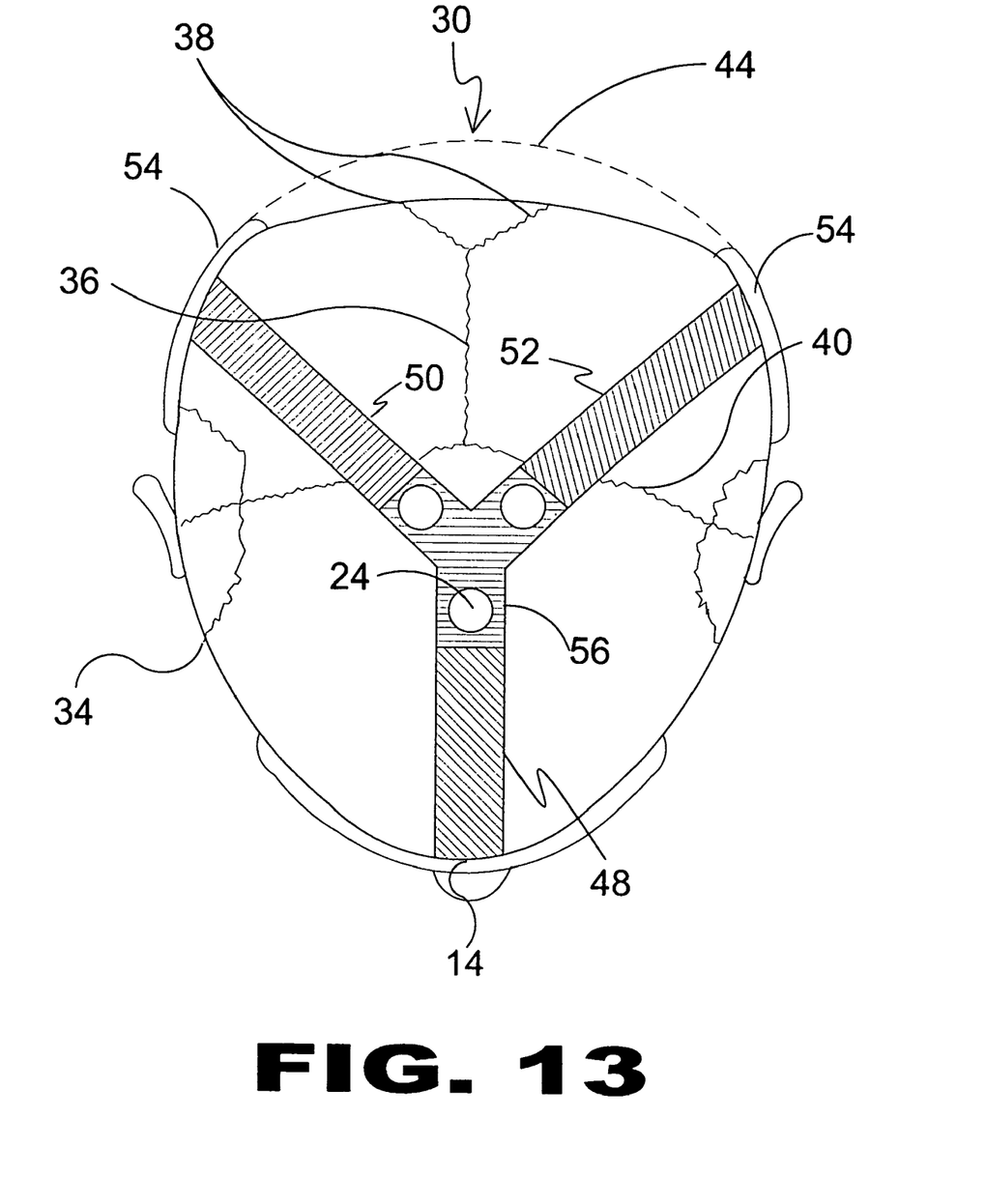
FIG. 13 is a top view of an additional element of the present invention.

Turning to FIG. 13, shown therein is a top view of an additional element of the present invention 10. Shown is a variation having intersecting straps 48, 50, 52 with pads 14, 54 positioned on each end forming a Y-design 56. The device 10 conforms to the contour of an infants head and is used to correct brachiocephaly, whereas the previous design is not applicable by redirecting the compressive forces that would otherwise be imposed on soft, compliant areas of the developing cranium. The device 10 discloses a cranial orthosis comprised of front 14 and lateral pads 54 incorporating means for adjusting pressure 24 thereon. Other previously disclosed elements are also shown.

I claim:

1. An apparatus for a cranial orthosis for treating positional plagiocephaly, comprising:

a) a frame member in the shape of an arc contoured to substantially fit the curvature of the cranium, said frame member having first and second free ends such that said ends are disposed substantially on opposite sides of the cranium, said frame member being sufficiently resilient to cause said ends to apply a desired pressure to the cranium;

b) wherein said frame member is adjustable in length so as to fit and apply the desired pressure to different sizes of cranium;

c) first and second pads being disposed on said first and second ends, respectively, of said frame member, said pads having inner and outer surfaces, said inner surface of each said pad being contoured to substantially fit the curvature of the cranium to permit correction of cranial deformities; and d) adjusting means in said frame member for adjusting the pressure applied by said pads on said cranium appropriately positioned to treat said positional plagiocephaly;

e) said frame member comprising telescoping male and female members, wherein said male end female members are slidably connected so that said frame member is adjustable in length, said adjusting means located where said male and female members overlap; and f) said adjusting means is a set screw to fix said frame members to retain a pressure selected for application by said pads.

2. The apparatus of claim 1, having means comprising a third removable pad joining said first and second pads for use during a sleep period to keep pressure off said cranial deformities and protect said cranium during said sleep period.

3. A method for treating positional plagiocephaly in a cranium comprising the steps of:

a) placing a frame member on said cranium, said frame member being in the shape of an arc contoured to substantially fit the curvature of the cranium, said frame member having first and second free ends such that said ends are disposed substantially on opposite sides of the cranium, said frame member having first and second pads disposed on said first and second ends, respectively, said pads having inner and outer surfaces, said inner surface of each said pad being contoured to substantially fit the curvature of the cranium, said frame member comprising separate segments joined at a junction between, said pads said pads being appropriately positioned to treat said positional plagiocephaly;

b) at said junction, adjusting pressure applied by said pads on said cranium for treatment of said positional plagiocephaly; and c) a third removable pad is attached during sleep to said first and second pads to protect said cranium against pressure on a deformity in said cranium.

* * * * *